(12) United States Patent
Ejima et al.

(10) Patent No.: US 9,872,499 B2
(45) Date of Patent: Jan. 23, 2018

(54) VIRUS-INACTIVATING COMPOSITION CONTAINING LOW-MOLECULAR WEIGHT COMPOUND AND ARGININE

(75) Inventors: Daisuke Ejima, Kawasaki (JP); Haruna Sato, Kawasaki (JP); Hajime Koyama, Wakayama (JP); Tsutomu Arakawa, Thousand Oaks, CA (US)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 13/591,839

(22) Filed: Aug. 22, 2012

(65) Prior Publication Data

US 2013/0035381 A1 Feb. 7, 2013

Related U.S. Application Data

(63) Continuation of application No. PCT/JP2011/055168, filed on Feb. 28, 2011.

(60) Provisional application No. 61/308,374, filed on Feb. 26, 2010.

(51) Int. Cl.
| | |
|---|---|
| A01N 47/44 | (2006.01) |
| A61K 31/192 | (2006.01) |
| A61K 31/198 | (2006.01) |
| A61K 31/222 | (2006.01) |
| A61K 31/341 | (2006.01) |
| A61K 31/352 | (2006.01) |
| A61K 36/82 | (2006.01) |
| A61K 45/06 | (2006.01) |

(52) U.S. Cl.
CPC ............ *A01N 47/44* (2013.01); *A61K 31/192* (2013.01); *A61K 31/198* (2013.01); *A61K 31/222* (2013.01); *A61K 31/341* (2013.01); *A61K 31/352* (2013.01); *A61K 36/82* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,137,922 | A * | 8/1992 | Shimamura et al. | 514/731 |
| 8,084,032 | B2 | 12/2011 | Yumioka et al. | |
| 2007/0212426 | A1 * | 9/2007 | Rath et al. | 424/638 |
| 2008/0318300 | A1 | 12/2008 | Koyama et al. | |
| 2009/0118352 | A1 | 5/2009 | Lu et al. | |
| 2009/0326031 | A1 | 12/2009 | Bonvila et al. | |
| 2011/0077384 | A1 | 3/2011 | Yumioka et al. | |
| 2012/0015424 | A1 | 1/2012 | Selvitelli et al. | |
| 2012/0142901 | A1 | 6/2012 | Yumioka et al. | |

FOREIGN PATENT DOCUMENTS

| | | | | |
|---|---|---|---|---|
| EP | 1958626 | A1 * | 8/2008 | ........... A23L 3/3508 |
| EP | 2046316 | | 4/2009 | |
| FR | 5695 | | 1/1968 | |
| JP | 2004091446 | A * | 3/2004 | |
| JP | 2009-263231 | | 11/2009 | |
| JP | 2012-509081 | | 4/2012 | |
| WO | WO 2004102655 | A1 * | 11/2004 | |
| WO | WO2011-105633 | | 9/2011 | |

OTHER PUBLICATIONS

Yamasaki et al. Journal of Pharmaceutical Sciences, vol. 97, No. 8, Aug. 2008. 3067-3073.*
Sugimoto et al. Antimicrob Agents Chemother. Jul. 1981; 20(1): 120-127.*
Furuya et al. International Journal of Molecular Medicine 22: 541-545, 2008.*
Katsuyama et al. nternational Journal of Pharmaceutics, vol. 361, No. 1-2 (2008 ) 92-98.*
Achilles, S. L., et al., "Microbicide Efficacy and Toxicity Tests in a Mouse Model for Vaginal Transmission of Chlamydia trachomatis," Sexually Transmitted Diseases, 2002;29:655-664.
Burke, Jr., T. R., et al., "Hydroxylated Aromatic Inhibitors of HIV-1 Integrase," J. Med. Chem. 1995;38:4171-4178.
Cone, R. A., et al., "Vaginal microbicides: detecting toxicities in vivo that paradoxically increase pathogen transmission," BMC Infectious Diseases 2006;6(90):1-16.
Cutler, B., et al., "Vaginal microbicides and the prevention of HIV transmission," Lancet Infectious Diseases 2008;8:685-697.
Furuya, A., et al., "Antiviral effects of ascorbic and dehydroascorbic acids in vitro," Int. J. Mol. Med. 2008;22:541-545.
Hemmerling, A., et al., "Lime Juice as a Candidate Microbicide? An Open-Label Safety Trial of 10% and 20% Lime Juice Used Vaginally," J. Women's Health 2007;16(7):1041-1051.
Hendrix, C. W., et al., "Topical Microbicides to Prevent HIV: Clinical Drug Development Challenges," Annu. Rev. Pharmacol. Toxicol. 2009;49:349-375.
Ho, H.-Y., et al., "Antiviral Effect of Epigallocatechin Gallate on Enterovirus 71," J. Agric. Food Chem. 2009;57:6140-6147.
Holmes, W., "Investigating widely available substances as vaginal microbicides," Sexual Health 2004;33:73-79.
Katsuyama, Y., et al., "Butyroyl-arginine as a potent virus inactivation agent," Int. J. Pharmaceutics 2008;361:92-98.
Keller, M. J., et al., " Topical microbicides for the prevention of genital herpes infection," J. Antimicrobial Chemotherapy 2005;55:420-423.
König, B., et al., "The Caffeoylics as a New Family of Natural Antiviral Compounds," Naturwissenschaften 1985;72:659-661.
Mayer, K. H., et al., "Safety and Tolerability of BufferGel, a Novel Vaginal Microbicide, in Women in the United States," Clinical Infectious Diseases 2001;32:476-482.
Song, J.-M., et al., "Antiviral effect of catechins in green tea on influenza virus," Antiviral Res. 2005;68:66-74.
Sugimoto, Y., et al., "N$^\alpha$-Cocoyl-L-Arginine Ethyl Ester, DL-Pyroglutamic Acid Salt, As an Inactivator of Hepatitis B Surface Antigen" Antimicrobial Agents and Chemotherapy 1979;16(3):329-332.

(Continued)

*Primary Examiner* — Amy L Clark

(74) *Attorney, Agent, or Firm* — Cermak Nakajima & McGowan LLP; Shelly Guest Cermak

(57) ABSTRACT

The invention provides a virus-inactivating composition with pH of 3.8 to 5.5, containing (A) 0.02 to 0.3 M arginine and (B) a component such as 0.01 to 10 mM flavonoid, polyphenol, or ascorbic acid derivative, 0.005 to 5 mass % of an arginine derivative, and 0.1 to 2.5 mass % of an extract solution of natural product.

1 Claim, No Drawings

(56) References Cited

OTHER PUBLICATIONS

Xiang, Y.-F., et al., "Current Status of Natural Products from Plants as Anti-herpes Simplex Virus 1 Agents," Virologica Sinica 2008;23(5):305-314.

Yamasaki, H., et al., "Arginine Facilitates Inactivation of Enveloped Viruses," J. Pharma. Sci. 2008;97(8):3067-3073.

International Search Report and Written Opinion for PCT Patent App. No. PCT/JP2011/055168 (dated Aug. 1, 2011).

Bliss, C. I., "The Toxicity of Poisons Applied Jointly", Annals of Applied Biology, vol. 26, No. 3, Aug. 28, 1939, pp. 585-615.

Delaney William E 4th et al., "Combinations of Adefovir With Nucleoside Analogs Produce Additive Antiviral Effects Against Hepatitis B Virus in Vitro", Antimicrobial Agents and Chemotherapy, American Society for Microbiology, Washington, DC, US, vol. 48, No. 10, Oct. 1, 2004, pp. 3702-3710.

Ji, C., et al., "CCR5 Small-Molecule Antagonists and Monoclonal Antibodies Exert Potent Synergistic Antiviral Effects by Cobinding to the Receptor", Molecular Pharmacology, American Society for Pharmacology and Experimental Therapeutics, US, vol. 72, No. 1, Jul. 1, 2007, pp. 18-28.

Langlet, J., et al., "Aggregation and surface properties of F-specific RNA phages: Implication for membrane filtration processes," Water Research, Elsevier, Amsterdam, NL, vol. 42, No. 10-11, May 1, 2008, pp. 2769-2777.

Office Action from European Patent App. No. 11708930.9 (dated Jun. 13, 2013).

Office Action from Japanese Patent App. No. 2012-538897 (dated Jan. 15, 2015).

\* cited by examiner

VIRUS-INACTIVATING COMPOSITION CONTAINING LOW-MOLECULAR WEIGHT COMPOUND AND ARGININE

This application is a Continuation of, and claims priority under 35 U.S.C. §120 to, International Application No. PCT/JP2011/055168, filed Feb. 28, 2011, and claims priority therethrough under 35 U.S.C. §119 to U.S. Provisional Patent Application No. 61/308,374, filed Feb. 26, 2010, the entireties of which are incorporated by reference herein.

TECHNICAL FIELD

The present invention relates to a virus-inactivating composition containing arginine and a particular low-molecular weight compound at particular concentrations. More specifically, the invention relates to a virus-inactivating composition highly capable of effectively inactivating viruses present on the skin and mucosal tissue of humans and animals without causing any problems, such as inflammatory disorders typically observed when conventional sterilizers are applied.

BACKGROUND ART

The use of prescription antiviral drugs, as well as the voluntary use of infection-preventing products which are readily and economically available are of importance when suppressing virus-induced infectious diseases which can spread infection on a large-scale among the humans and animals, making them critically ill and attacking the economy (Annu. Rev. Pharmacol. Toxicol. 49, 349-375 (2009)).

Such individual and voluntary preventive measures will become effective, especially against infection of influenza virus, herpes virus, HIV and the like because those viruses can be inactivated relatively easily although they are highly infectious. Based on the above-mentioned concept, several clinical surveys were conducted among the subjects at high risk of HIV infection in the African countries in order to verify the prevention of HIV infection by using sterilizers which contain a surfactant as the main ingredient and are available without any medical prescription at reasonable prices. Although HIV was inactivated temporarily, those studies ended in tragedy because the mucosal tissues of the subjects became inflamed, which unfortunately accelerated the HIV infection (BMC Infectious Disease 6: 90 (2006); Lancet Infectious Disease 8, 685-697 (2008); and Journal of Antimicrobial Chemotherapy 55, 420-423 (2005)).

In general, surfactants can effectively inactivate the viruses, while the tending to induce an immune response of the living organism by the tissue damaging property. The use of surfactants is therefore extremely limited in the diseases where viruses are increasing on the mucosal tissue.

It has been also hitherto believed in the Western countries that very familiar acidic foods such as table vinegar, lemon juice, lime juice and the like can be used to inactivate viruses and prevent infectious diseases. Recently, clinical tests were conducted to verify the effects and safety of this hypothesis. According to the reports, these acidic foods have little effect on the prevention of infectious diseases. On the contrary, it has been found that side effects are conspicuously induced, for example, introduction of new infectious diseases, occurrence of acute disorders, and the like (Journal of Woman's Health 16, 1041-1051 (2007); and Sexual Health 33, 73-79 (2004)). Another treatment is local administration of *lactobacilli*, which has been hitherto believed to be a safe and specific remedy. This treatment aims to enhance the effect of protecting the mucosal tissue by using a peptide factor produced by *lactobacilli* and the obtained acidic pH. However, the above-mentioned treatment has been found to involve unexpected risks, such as development of infectious diseases caused by the pathogenic microbes mixed in the *lactobacilli*, activation of the tissue-derived factors to accelerate the growth of HIV by the action of *lactobacilli*, and the like (Sexual Health 33, 73-79 (2004)). In the clinical studies aiming to prevent HIV infection, to protect the mucosal tissue from virus- and microbe-infection using an acidic pH environment as the tissue takes advantage of *lactobacilli* flora, some attempts are now in progress to ensure a stronger and stabler acidic environment by local administration of a gel containing an acidic buffer (Clinical Infectious Diseases 32, 476-482 (2001)).

Those tests aim at finding a so-called mucosal environment protection enhancer. As yet no conclusion has been reached in regard to whether the acidic buffer-containing gel itself works to inactivate the viruses based on the generated acidic pH environment. It has been reported that the acidic pH does not in fact function and is a physical barrier of the gel that effectively works (Sexually Transmitted Diseases 29, 655-664 (2002)).

In Chinese medicine, many examples have been reported of natural products derived from particular plants and animals that can highly inactivate viruses or highly suppress the growth of viruses in the virus-infected cell or tissue. There is much research being conducted to look for natural products capable of inactivating viruses (Virologica Sinica 23, 305-314 (2008)).

However, it is not easy to find an ingredient that can produce the virus-inactivating effect and is safe for the living body, even if the ingredient is derived from natural products. In most cases, the acting mechanism of those active natural products has not yet been ascertained, which inhibit the development of those ingredients derived from natural products as therapeutics for infectious diseases or infection inhibitors (Virologica Sinica 23, 305-314 (2008)).

Arginine, one of the amino acids found in the living body, is a remarkably safe ingredient and also is known to exhibit an effective virus-inactivating effect by appropriately adjusting its concentration and pH (Japanese Patent Unexamined Publication ("JP Kokai") No. 2009-263231; Journal of Pharmaceutical Sciences, 97, 3067-3073 (2008); and International Journal of Pharmaceutics 361, 92-98 (2008)).

SUMMARY OF INVENTION

It is an aspect of the invention is to provide a composition capable of effectively inactivating viruses which are proliferating on the outer surface of the tissue, or easily inactivating viruses which remain on the surface of substrates or the like, without damaging the skin and the mucosal tissue of humans and animals.

A composition is described which contains arginine in combination with well-known low molecular weight compounds including polyphenols, flavonoids and ascorbic acid derivatives, arginine derivatives or an extract solution of natural product at the particular concentrations within the particular pH range.

It is an aspect of the present invention to provide a composition comprising (A) 0.02 to 0.3 M arginine and (B) a component selected from the group consisting of:

i) 0.01 to 10 mM flavonoid, polyphenol, or ascorbic acid derivative, ii) 0.005 to 5 mass % of an arginine derivative, and iii) 0.1 to 2.5 mass % of an extract solution of natural product;

wherein said composition is able to inactivate one or more viruses, and has a pH of 3.8 to 5.5.

It is a further aspect of the present invention to provide a method of inactivating one or more viruses comprising bringing a composition having pH of 3.8 to 5.5 into contact with one or more viruses, the composition comprising (A) 0.02 to 0.3 M arginine and (B) a component selected from the group consisting of:

i) 0.01 to 10 mM flavonoid, polyphenol or ascorbic acid derivative, ii) 0.005 to 5 mass % of an arginine derivative, and iii) 0.1 to 2.5 mass % of an extract solution of natural product.

Each component of the composition can be at a low concentration, so that each component does not have a strong physiological effect on the living tissue. Therefore, it is possible to inactivate viruses effectively without any concern about side effects such as damage to the tissue or the like. The invention can also inactivate viruses which are proliferating on the outer surface of the living tissue without inducing disorders in the humans and animals. Also, the invention can quickly inactivate viruses remaining on the surface of substrates which may come in contact with the living tissue, such as on the surface of a solid such as plant tissue or the like; present in liquids such as pharmaceuticals in the form of a solution, syrup or the like, and present in foods in a liquid form, for example, beverages, mayonnaise and the like; or present in gases such as air or the like, without exerting any adverse effect on the surrounding tissue and the characteristics of the individual.

DESCRIPTION OF THE PREFERRED EMBODIMENTS

The composition can include particular amounts of (A) arginine and (B) a component such as i) flavonoid, polyphenol or ascorbic acid derivative; ii) an arginine derivative, or iii) an extract solution of natural product. The extract solution of natural product is one particular example of the second component.

(A) Arginine

Arginine in the virus-inactivating composition can be effective in virus inactivation when contained at a concentration of 0.02 M or more. The upper limit of the arginine concentration can be 0.3 M, in consideration of the effectiveness in virus inactivation and economy. The arginine concentration can be 0.03 to 0.25 M, or 0.05 to 0.2 M.

Both the L-form and the D-form of arginine can be used. It is also possible to use arginine in the form of an acid addition salt. Examples of the acid that can be used to form the acid addition salts can include hydrochloric acid, sulfuric acid and the like.

Flavonoids, polyphenols or ascorbic acid derivatives

The concentration of the flavonoid, polyphenol or ascorbic acid derivative in the virus-inactivating composition can be reduced to such a low level that there are few adverse effects, such as stimuli to living organisms, cytotoxicity, and the like. More specifically, the concentration can be in the range of 0.01 to 10 mM, 0.02 to 5 mM, or 0.05 to 1 mM. The term "polyphenols" can be generally defined to include flavonoids, so that the term "polyphenols" can be polyphenols other than flavonoids.

The flavonoids, polyphenols and ascorbic acid derivatives have many known uses, and there are many products containing these ingredients which are approved as pharmaceuticals, pharmaceutical additives, quasi-drug additives, or food additives. For example, the following can be used:

Examples of the flavonoids can include (−)epicatechin gallate, (−)epigallocatechin gallate, (−)epigallocatechin, (−)epicatechin, (−)gallocatechin gallate, and the like. Particular examples are (−)epicatechin gallate and (−)epigallocatechin gallate.

Examples of the polyphenols can include caffeic acid, caffeic acid phenethyl ester, tannin, sesamin, sesaminol, and their salts with bases. Examples of the bases for forming the salts include sodium hydroxide, potassium hydroxide, and the like. Particular examples are caffeic acid and caffeic acid phenethyl ester.

Examples of the ascorbic acid derivatives can include dehydroascorbic acid, L-ascorbic acid phosphate, esters such as ascorbic acid glucoside, ascorbyl stearate, ascorbic acid-2-O-phosphate-6-O-palmitate, and their salts with bases. Examples of the bases for forming the salts include sodium hydroxide, potassium hydroxide, and the like. In particular, dehydroascorbic acid is one particular example.

Arginine Derivatives

The concentration of the arginine derivatives in the virus-inactivating composition can be in the range of 0.005 to 5%. When the corresponding arginine derivative has the property of surface activity, the arginine derivative can become effective at a concentration of 0.005% or more. However, when the arginine derivative is used at higher concentrations than necessary, the derivative may become irritating. In light of this, the concentration may be in the range of 0.005 to 0.5%, 0.0075 to 0.25%, or 0.01 to 0.1%. When the corresponding arginine derivative does not have any surface activity, the concentration can be in the range of 0.2 to 5%, or 0.5 to 3%.

Many arginine derivatives are approved as pharmaceuticals, pharmaceutical additives, food additives or raw materials for cosmetics and toiletries. Examples of the arginine derivatives can include acyl arginine having an acyl chain with 8 to 16 carbon atoms and the salts thereof with acids or bases. As the acids for forming the salts, hydrochloric acid and the like can be employed. As the bases for forming the salts, sodium hydroxide and the like can be employed. Specific examples of the acyl arginine having an acyl chain with 8 to 16 carbon atoms include cocoyl arginine ethyl ester, lauroyl arginine ethyl ester and the like. In particular, cocoyl arginine ethyl ester and lauroyl arginine ethyl ester are particular examples.

Extract Solution of Natural Products

Some extract solutions of natural products can contain at least one of flavonoids, polyphenols or ascorbic acid derivatives and can also be used. For example, the extract solution of green tea is known to contain flavonoids, that is, catechins at high concentrations. It is reported that the total content of the main four catechin derivatives, i.e., epigallocatechin gallate, epicatechin gallate, epigallocatechin, and epicatechin in the green tea extract solution is about 0.3% (FFI Reports, Feb. 25, 2010 (access: www.saneigenffi.co.jp/foods/img1/catechin.pdf). When the extract solution of green tea is added in the virus-inactivating composition, the content of the extract solution of natural product may be adjusted to 0.1 to 2.5%, 0.2 to 1.5%, or 0.4 to 1.2%. This corresponds to 0.0003 to 0.0075% when converted into the content of the main catechins in the composition, which can also be expressed as 0.007 to 0.175 mM in terms of the molar concentration. The above-mentioned concentration is lower than that as previously explained with respect to the group of flavonoids, polyphenols or ascorbic acid derivatives. Without wishing to be bound by any theory, in the extract solution of the natural product, any other catechins, polyphenols other than catechins, ascorbic acids and the like can be contained in addition to the main catechins, and are expected to exhibit a further strong effect when used in combination with the main catechins.

As the extract solution of natural product, a variety of plant extracts and essential oils may be blended. Examples of the plant extracts are green tea extract, black tea extract, tea extract, houttuynia extract, phellodendron bark extract, sweet clover extract, lamium album extract, glycyrrhiza extract, paeony root extract, saponaria extract, sponge gourd extract, cinchona extract, saxifrage extract, sophora root extract, nuphar extract, fennel extract, primula veris extract, rose extract, rehmannia root extract, lemon extract, lithospermum root extract, aloe extract, calamus rhizome extract, eucalyptus extract, horsetail extract, sage extract, thyme extract, seaweed extract, cucumber extract, clove extract, raspberry extract, balm mint extract, ginseng extract, carrot extract, horse chestnut extract, peach extract, peach leaf extract, mulberry bark extract, cornflower extract, witch hazel extract, silk extract, yarrow extract, hop extract, rosemary extract, bitter orange peel extract, citrus unshiu peel extract, hypericum extract, citrus junos fruit extract, citrus aurantium fruit extract, gleditsia japonica extract, loquat leaf extract, honeysuckle extract, angelica dahurica root extract, linden extract, horse chestnut extract, mugwort extract, chamomile extract, cinnamon bark extract, and the like.

Examples of the essential oils include mint oil, jasmine oil, camphor oil, hinoki oil, citrus aurantium oil, *nephelium longana* seed extract, turpentine oil, cinnamon oil, bergamot oil, orange oil, *Acorus calamus* oil, pine oil, lavender oil, bay laurel oil, clove oil, Hiba oil, rose oil, eucalyptus oil, lemon oil, thyme oil, pepper mint oil, sage oil, menthol, cineol, eugenol, citral, citronellal, borneol, linalool, geraniol, camphor, thymol, spilanthol, pinene, limonene, terpene compounds, and the like.

As the extract solution of natural product, green tea extract solution is one particular example. For example, it is possible to use a green tea extract solution obtainable by immersing 60 g of tea leaves of green tea into hot water of 90° C. for five minutes and then removing the tea leaves. Alternatively, it is also possible to use a green tea extract solution obtainable by extracting green tea leaves with 30 to 50 vol. % of ethanol and removing the tea leaves in the same manner as in the above. The green tea extract solutions thus obtained contain the main catechins as mentioned above in an amount of about 0.3%.

Using a proper buffer solution constituent, the virus-inactivating composition of the invention can be adjusted to pH 3.8 to 5.5, 3.9 to 5.3, or 4.0 to 4.8, when measured at 25° C. When the arginine derivative has the property of surface activity, the pH range may be adjusted from a slightly acidic region to a neutral region of more than 5.5 so that the virus inactivating effect can be obtained without causing any stimulating action. However, to allow the arginine derivative to exhibit the effectiveness at lower concentrations, the pH range may be desirably adjusted to 5.5 or less.

Examples of the buffer solution constituent that can be used to adjust the pH can include lactic acid, sodium lactate, citric acid, sodium citrate, glycollic acid, succinic acid, tartaric acid, dl-malic acid, boric acid, borax, sodium hydrogen phosphate, 2-amino-2-methyl-1-propanol, 2-amino-2-methyl-1,3-propanediol, sodium hydride, potassium hydride, triethanolamine, potassium carbonate, sodium hydrogen carbonate, ammonium hydrogen carbonate, and the like. The buffer solution constituent may be free of calcium or magnesium so as not to form a precipitate.

The virus-inactivating composition may further contain any ingredients that are generally approved for use in pharmaceuticals, quasi-drugs, cosmetics or foods to such an extent that the effect of virus inactivation is not be impaired. Examples of those ingredients include a preservative, an anti-inflammatory agent, a humectant, an antioxidant, a chelating agent and the like.

Specific examples of the preservative can include phenoxyethanol, bisabolol, benzoic acid, salicylic acid, phenol, sorbic acid, p-hydroxy benzoic acid ester, p-chloro-m-cresol, hexachlorophene, benzalkonium chloride, benzethonium chloride, chlorhexidine chloride, trichlorocarbanilide, triclosan, isopropylmethylphenol, photosensitizers, and the like.

Specific examples of the anti-inflammatory agent can include guaiazulene, sodium guaiazulene sulfonate, ethyl guaiazulene sulfonate, glycyrrhetinic acid, glyceryl glycyrrhetinate, stearyl glycyrrhetinate, pyridoxine glycyrrhetinate, glycyrrhetinyl stearate, disodium 3-succinoyl glycyrrhetinate, glycyrrhizic acid, monoammonium glycyrrhizinate, dipotassium glycyrrhizinate, trisodium glycyrrhizinate, allantoin, aminocaproic acid, lysozyme chloride, and the like.

Specific examples of the humectant can include polyethylene glycol, propylene glycol, dipropylene glycol, 1,3-butylene glycol, pentanediol, hexylene glycol, octanediol, erythritol, xylitol, maltitol, maltose, mannite, malt sugar, glucose, fructose, lactose, sodium chondroitin sulfate, sodium hyaluronate, sodium adenosine phosphate, sodium lactate, bile acid salts, pyrrolidone carboxylic acid salts, glucosamine, cyclodextrin, trehalose, and the like.

In addition to the above, amino acids and the derivatives thereof can also be used as the humectant. Specific examples can include aliphatic and aromatic neutral, acidic and basic amino acids such as glycine, serine, threonine, phenylalanine, cysteine, methionine, aspartic acid, glutamic acid, histidine, arginine, proline, and the like. Those may be used in the form of salts, for example, sodium salts, potassium salts, triethanolamine salts, and the like. The derivatives of amino acids can include, for example, acetylglutamic acid, acetylmethionine, acetylcysteine, N,N'-diacetyl-L-cystinedimethyl ester, sodium pyrrolidone carboxylate, and the like.

Specific examples of the antioxidant can include dibutylhydroxytoluene, butylhydroxyanisole, propyl gallate, ascorbic acid, and the like.

Specific examples of the chelating agent can include disodium edetate, ethanehydroxy diphosphate, pyrophosphate, hexamethaphosphate, citric acid, tartaric acid, gluconic acid, and the like.

The virus-inactivating composition may further contain fats and oils, emulsifiers and high-molecular compounds if needed for the formulation.

Examples of the fats and oils can include liquid products such as meadowfoam oil, macadamia nut oil, *camellia* oil, corn oil, mink oil, olive oil, avocado oil, *camellia oleifera* seed oil, castor oil, safflower oil, apricot kernel oil, jojoba oil, grape seed oil, sunflower oil, almond oil, rape seed oil, sesame oil, wheat germ oil, rice germ oil, rice bran oil, cotton seed oil, soybean oil, peanut oil, tea seed oil, evening primrose oil, egg yolk oil, triglycerin, glycerol trioctanoate, glycerol triisopalmitate, and the like; and solid products such as cetanol, cetostearyl alcohol, stearyl alcohol, behenyl alcohol, cocoa butter, coconut oil, palm oil, palm kernel oil, hardened oil, hydrogenated castor oil, japan wax, shea butter, and the like.

Examples of the waxes can include beeswax, candelilla wax, cotton wax, carnauba wax, spermaceti, rice bran wax, lanolin, hydrogenated lanolin, lanolin wax, jojoba wax, shellac wax, and the like.

Examples of the ester oils can include octanoates such as cetyl octanoate and the like, laurates such as hexyl laurate and the like, myristates such as isopropyl myristate, octyldodecyl myristate and the like, palmitates such as octyl palmitate and the like, stearates such as isocetyl stearate and the like, isostearates such as isopropyl isostearate and the like, isopalmitates such as octyl isopalmitate and the like, oleates such as isodecyl oleate and the like.

Examples of the hydrocarbon oils can include liquid paraffin, ozokerite, squalane, paraffin, isoparaffin, ceresin, vaseline, microcrystalline wax, and the like.

Examples of the silicone oils can include linear silicones such as dimethyl polysiloxane, methylphenyl polysiloxane and the like; and cyclic silicones such as octamethyl cyclotetrasiloxane, decamethyl cyclopentasiloxane, dodecamethyl cyclohexasiloxane, and the like.

Examples of the sterols can include cholesterol, sitosterol, phytosterol, lanosterol, and the like.

Examples of the emulsifiers can include POE sorbitan fatty acid esters such as POE sorbitan monooleate, POE sorbitan monostearate, POE sorbitan monooleate, POE sorbitan tetraoleate and the like; POE sorbit fatty acid esters such as POE sorbit monolaurate, POE sorbit monooleate, POE sorbit pentaoleate, POE sorbit monostearate and the like; POE glycerol fatty acid esters such as POE glycerol monostearate, POE glycerol monoisostearate, POE glycerol triisostearate and the like; POE fatty acid esters such as POE monooleate, POE distearate, POE monodioleate, ethylene glycol distearate and the like; POE alkyl ethers such as POE lauryl ether, POE oleyl ether, POE stearyl ether, POE behenyl ether, POE 2octyldodecyl ether, POE cholestanol ether, and the like; POE alkylphenyl ethers such as POE octylphenyl ether, POE nonylphenyl ether, POE dinonylphenyl ether and the like; pluaronic types such as Pluronic; and POE.POP alkyl ethers such as POE.POP cetyl ether, POE.POP 2 decyltetradecyl ether, POE.POP monobutyl ether, POE.POP hydrogenated lanolin, POE.POP glycerol ether and the like; POE castor oil and POE hydrogenated castor oil derivatives including POE castor oil, POE hydrogenated castor oil, POE hydrogenated castor oil monoisostearate, POE hydrogenated castor oil triisostearate, POE hydrogenated castor oil monopyroglutamic acid monoisostearic acid diester, POE hydrogenated castor oil maleic acid, and the like; POE beeswax.lanolin derivative such as POE sorbit beeswax; sucrose esters of fatty acids, trioleyl phosphate, and the like.

Examples of the high molecular weight compounds can include water-soluble plant-derived polymers such as gum arabic, guar gum, karaya gum, carrageenan, pectin, quince seed (*Cydonia oblonga*), starch (rice, corn, potato, wheat), alge colloid (Phaeophyceae extract), and the like; microorganism-derived polymers such as dextran, succinoglucan, pullulan and the like; animal-derived polymers such as collagen, casein, albumin, gelatin and the like; starch-derived polymers such as carboxymethyl starch, methylhydroxy propyl starch and the like; cellulose polymers such as methyl cellulose, nitrocellulose, ethyl cellulose, methylhydroxy propyl cellulose, hydroxyethyl cellulose, cellulose sulfate sodium salt, hydroxypropyl cellulose, carboxymethyl cellulose sodium salt, microcrystalline cellulose, cellulose powder and the like; alginic acid based polymers such as sodium alginate, propylene glycol alginate and the like; vinyl polymers such as carboxyvinyl polymer, alkyl-modified carboxyvinyl polymer and the like; polyoxyethylene polymers; polyoxyethylene polyoxypropylene copolymers; acrylic polymers such as poly(sodium acrylate), poly(ethyl acrylate), polyacrylamide and the like; and water-soluble inorganic polymers such as bentonite, magnesium aluminum silicate, laponite, hectorite, silicic anhydride, and the like.

The virus-inactivating composition can further contain a proper perfume, coloring agent and the like when necessary as long as the transparency and the stability is not impaired.

The virus-inactivating composition can be brought into contact with a solid object which has been contaminated with one or more viruses by spraying using a spray equipment or coating with a brush or the like. Alternatively, a non-woven fabric impregnated with the virus-inactivating composition may be applied onto a target portion or inserted between a mask and a person wearing the mask. When the virus-inactivating composition is brought into contact with a liquid that may be contaminated with viruses, the liquid and the composition can be stirred or mixed together as necessary. The means for stirring or mixing is not particularly limited. When the above-mentioned liquid is an oily substance such as oil or fat, an emulsifier may be added for complete contact of the liquid with the composition. Any emulsifiers as previously mentioned may be used.

In the invention, the target virus for inactivation is not particularly limited, but includes, for example, influenza virus, herpes virus, rhinovirus, and coronavirus. The present invention can is particularly effective on viruses having lipid envelope.

Unless otherwise specified, the term "%" can mean the percent by mass based on the total mass of the virus-inactivating composition.

The present invention will be further explained by reference to the following non-limiting examples.

EXAMPLES

Example 1

Increase of the Virus-Inactivating Effect by Using a Low Molecular Weight Polyphenolic Compound (Caffeic Acid) in Combination with Arginine Vero cells were grown in Eagle's minimum essential medium (MEM) supplemented with 0.5% fetal calf serum, to propagate herpes simplex virus type 1 (HSV-1) strain F. A highly concentrated virus solution was thus prepared. The virus solution was stored at −80° C. until use. The virus concentration of the virus solution was about $10^8$ plaque forming units (PFU)/ml.

Using caffeic acid (Sigma-Aldrich Corporation) and arginine, sample solutions having various concentrations as shown in Table 1 were prepared. All the sample solutions were adjusted to pH 4.0 (25° C.) using 20 mM sodium acetate buffer solution.

While cooled with ice, 190 µl of each sample solution was transferred to a plastic tube (Assist tube, 1.5 ml). To each sample solution, 10 µl of the HSV-1 virus solution prepared as mentioned above was added, and immediately stirred and mixed to initiate the virus inactivating reaction. Then, each solution was maintained at 30° C. for 5 minutes. Five minutes later, the virus inactivating reaction was terminated by diluting 100 times with Dulbecco's phosphate buffer solution containing 1% fetal calf serum (not containing Ca and Mg) for neutralization. The reaction solution thus obtained was appropriately diluted with Dulbecco's phosphate buffer solution containing 1% fetal calf serum (not containing Ca and Mg), and then the number of infectious viruses (remaining viral amount) was determined using a plaque assay (Virus Res. 13, 271-282 (1989)).

On the other hand, 10 μl of the same virus solution as mentioned above was added to 190 μl of Dulbecco's phosphate buffer solution (not containing Ca and Mg), followed by maintaining at 30° C. for 5 minutes. Five minutes later, the number of infectious viruses was determined using the same plaque assay as mentioned above. The number of viruses thus determined was regarded as the viral amount obtainable without the virus inactivating reaction, that is, the viral amount before inactivation.

After an attempt to inactivate the viruses by using 0.1 mM caffeic acid alone, the viral titer was reduced to 0.3% of the viral amount before inactivation. The inactivating efficiency obtained by each of the sample solutions was expressed as a value relative to the above-mentioned inactivating efficiency obtained by using 0.1 mM caffeic acid alone. The results are shown in Table 1.

When the sample solutions containing caffeic acid alone at concentrations of 0.1, 0.5 and 1.0 mM were used, the inactivating efficiencies were no more than 1 to 1.4 times. There was no concentration-dependent increase in inactivating efficiency when caffeic acid was used.

In contrast to this, when 0.2 M arginine was added to each solution, the inactivation increased depending on the concentration of caffeic acid. When the concentration of caffeic acid was 1 mM, the inactivating efficiency went up to 7.8 times as high as the initial inactivating efficiency. In other words, it was found that caffeic acid can first inactivate the viruses in a concentration-dependent manner when arginine is present in the virus solution.

TABLE 1

Virus-inactivating effect by using caffeic acid and arginine in combination

| Compound Name | Concentration of Compound (mM) | Concentration of Arginine (M) | Relative Inactivating Efficiency (times) |
|---|---|---|---|
| Caffeic acid | 0.1 | 0 | 1 |
| Caffeic acid | 0.5 | 0 | 1.3 |
| Caffeic acid | 1 | 0 | 1.4 |
| Caffeic acid | 0.1 | 0.2 | 1.5 |
| Caffeic acid | 0.5 | 0.2 | 3.3 |
| Caffeic acid | 1 | 0.2 | 7.8 |

Example 2

Increase of the Virus-Inactivating Effect by Using a Low Molecular Weight Polyphenolic Compound (Caffeic Acid Phenethyl Ester) in Combination with Arginine The virus inactivating efficiency of each sample solution was determined in the same manner as in Example 1 except that caffeic acid was replaced by caffeic acid phenethyl ester (Sigma-Aldrich Corporation) and the concentration thereof was changed as shown in Table 2.

The inactivating efficiency obtained by each sample solution was expressed as a value relative to the inactivating efficiency obtained by using 0.01 mM caffeic acid phenethyl ester alone. The results are shown in Table 2.

When 0.01 mM caffeic acid phenethyl ester was used alone for inactivation, the remaining viral titer was decreased to 0.3% of that obtained before inactivation. In this case, the virus inactivating efficiency was not changed at all even when the concentration of caffeic acid phenethyl ester was increased up to 0.1 mM.

In contrast, when 0.2 M arginine was added to each sample solution, the inactivating efficiency increased depending on the concentration of caffeic acid phenethyl ester. When the concentration of caffeic acid phenethyl ester was 0.1 mM, the inactivating efficiency went up to more than 243 times the initial inactivating efficiency. In other words, it was found that caffeic acid phenethyl ester can first inactivate the viruses in a concentration-dependent manner when arginine is present in the virus solution.

TABLE 2

Virus-inactivating effect by using caffeic acid phenethyl ester and arginine in combination

| Compound Name | Concentration of Compound (mM) | Concentration of Arginine (M) | Relative Inactivating Efficiency (times) |
|---|---|---|---|
| Caffeic acid phenethyl ester | 0.01 | 0 | 1 |
| Caffeic acid phenethyl ester | 0.05 | 0 | 1 |
| Caffeic acid phenethyl ester | 0.1 | 0 | 1 |
| Caffeic acid phenethyl ester | 0.01 | 0.2 | 8 |
| Caffeic acid phenethyl ester | 0.05 | 0.2 | 122 |
| Caffeic acid phenethyl ester | 0.1 | 0.2 | >243 |

Example 3

Increase of the Virus-Inactivating Effect by Using Ascorbic Acid Derivative in Combination with Arginine The virus inactivating efficiency of each sample solution was determined in the same manner as in Example 1 except that caffeic acid was replaced by dehydroascorbic acid (made by Wako Pure Chemical Industries, Ltd.) and the concentration thereof was changed as shown in Table 3. The inactivating efficiency obtained by each sample solution was expressed as a value relative to the inactivating efficiency obtained by using 0.1 mM dehydroascorbic acid alone. The results are shown in Table 3.

When 0.1 mM dehydroascorbic acid was used alone for inactivation, the remaining viral titer was decreased to 7.3% of the viral amount before inactivation. In this case, the virus inactivating efficiency was not changed at all even by increasing the concentration of dehydroascorbic acid up to 10 mM.

In contrast to this, when 0.2 M arginine was added to each solution, the inactivating efficiency increased depending on the concentration of dehydroascorbic acid. When the concentration of dehydroascorbic acid was 10 mM, the inactivating efficiency went up to more than 7200 times the initial inactivating efficiency. In other words, it was found that dehydroascorbic acid can first inactivate the viruses in a concentration-dependent manner when arginine was present in the virus solution together with arginine.

TABLE 3

Virus-inactivating effect by using dehydroascorbic acid and arginine in combination

| Compound Name | Concentration of Compound (mM) | Concentration of Arginine (M) | Relative Inactivating Efficiency (times) |
|---|---|---|---|
| Dehydroascorbic acid | 0.1 | 0 | 1 |
| Dehydroascorbic acid | 1 | 0 | 1 |
| Dehydroascorbic acid | 10 | 0 | 1 |
| Dehydroascorbic acid | 0.1 | 0.2 | 248 |
| Dehydroascorbic acid | 1 | 0.2 | 1440 |
| Dehydroascorbic acid | 10 | 0.2 | >7200 |

Example 4

Increase of the Virus-Inactivating Effect by Using Catechins in Combination with Arginine The virus inactivating efficiency of each sample solution was determined in the same manner as in Example 1 except that caffeic acid was replaced by (−)epicatechin gallate or (−)epigallocatechin gallate (Wako Pure Chemical Industries, Ltd.) and the concentrations thereof were changed as shown in Table 4. The inactivating efficiency obtained by each sample solution was expressed as a value relative to the inactivating efficiency separately obtained by using 0.1 mM (−)epicatechin gallate or (−)epigallocatechin gallate alone. The results are shown in Table 4.

When 0.1 mM (−)epicatechin gallate was used alone for inactivation, the remaining viral titer was decreased to 0.04% of the viral amount before inactivation. When 0.1 mM (−)epigallocatechin gallate was used alone for inactivation, the amount of viruses that remained was decreased to 0.02% of the viral amount before inactivation. The (−)epicatechin gallate and (−)epigallocatechin gallate allowed the virus inactivating efficiency to respectively rise 27 times and 268 times the initial inactivating efficiency when the concentration was increased to 0.5 mM.

When 0.2 M arginine was added to the 0.1 mM (−)epicatechin gallate solution, the inactivating efficiency increased 59 times the efficiency obtained without arginine. In the case where 0.2 M arginine was added to the 0.5 mM (−)epicatechin gallate solution, the inactivating efficiency went up to as high as more than 6408 times the initial efficiency. When 0.2 M arginine was added to the 0.1 mM (−)epigallocatechin gallate solution, the inactivating efficiency increased 12 times the initial efficiency. In the case where 0.2 M arginine was added to the 0.5 mM (−)epigallocatechin gallate solution, the inactivating efficiency went up to as high as more than 2650 times the initial efficiency. In other words, it was found that addition of arginine can drastically enhance the inactivating effect of the catechins.

TABLE 4

Virus-inactivating effect by using catechins and arginine in combination

| Compound Name | Concentration of Compound (mM) | Concentration of Arginine (M) | Relative Inactivating Efficiency (times) |
|---|---|---|---|
| (−)epicatechin gallate | 0.1 | 0 | 1 |
| (−)epicatechin gallate | 0.5 | 0 | 27 |
| (−)epicatechin gallate | 0.1 | 0.2 | 59 |
| (−)epicatechin gallate | 0.5 | 0.2 | >6408 |
| (−)epigallocatechin gallate | 0.1 | 0 | 1 |
| (−)epigallocatechin gallate | 0.5 | 0 | 268 |
| (−)epigallocatechin gallate | 0.1 | 0.2 | 12 |
| (−)epigallocatechin gallate | 0.5 | 0.2 | >2650 |

Example 5

Increase of the Virus-Inactivating Effect by Using Green Tea Extract Solution in Combination with Arginine NDCK cells were grown in Eagle's minimum essential medium (MEM) supplemented with 0.1% bovine serum albumin and 4 μg/ml acetylated trypsin, to propagate influenza virus A/Aichi (H3N2). A highly concentrated virus solution was thus prepared. The virus solution was stored at −80° C. until use. The virus concentration of the virus solution was about $10^8$ PFU/ml.

A commercially available green tea extract solution (Lot Number 9095671J1, made by Maruzen Pharmaceuticals Co., Ltd.) was adjusted to pH 4.0 (25° C.) by diluting 20 times with 20 mM sodium acetate buffer solution of pH4.0. The green tea extract dilute solution was further diluted with 10 mM sodium citrate buffer solution to have a final concentration within a range from 0.1 to 2.5%.

The green tea extract dilute solutions having various concentrations thus obtained were adjusted to pH4.2 or pH4.8, so that arginine-free sample solutions were prepared. On the other hand, arginine was added to each of the green tea extract dilute solutions having various concentrations so as to have an arginine concentration of 0.115 M, followed by pH adjustment to 4.2 or 4.8 (25° C.). Thus, arginine-containing sample solutions were prepared.

Under ice-cooling condition, 190 μl of each sample solution was transferred to a plastic tube (Assist tube, 1.5 ml). To each sample solution, 10 μl of the influenza virus A solution prepared as mentioned above was added, and immediately stirred and mixed to initiate the virus inactivating reaction. Then, each solution was maintained at 30° C. for 5 minutes. Five minutes later, the virus inactivating reaction was terminated by diluting 100 times with Dulbecco's phosphate buffer solution containing 0.1% bovine serum albumin (not containing Ca and Mg) for neutralization. The reaction solution thus obtained was appropriately diluted with Dulbecco's phosphate buffer solution containing 0.1% bovine serum albumin (not containing Ca and Mg), and then the number of infectious viruses (remaining viral titer) was determined using a plaque assay in the same manner as for the plaque assay using MDCK cells (Intern. J. Mol. Med. 3, 527-530 (1999)).

On the other hand, 10 μl of the same virus solution as mentioned above was added to 190 μl of Dulbecco's phosphate buffer solution (not containing Ca and Mg), and the mixture was maintained at 30° C. for 5 minutes. Five minutes later, the number of infectious viral titer was determined using the same plaque assay as mentioned above. The number of viruses thus determined was regarded as the viral amount obtainable without the virus inactivating reaction, that is, the viral titer before inactivation.

After the inactivation was carried out using 0.1% green tea extract solution of pH 4.2 alone, the viral amount was reduced to 0.1% of the viral amount before inactivation. After the inactivation was carried out using 0.1% green tea extract solution of pH 4.8 alone, the viral amount was reduced to 1.5% of the viral amount before inactivation. The inactivating efficiency obtained by each sample solution was expressed as a value relative to the above-mentioned inactivating efficiency obtained by using the green tea extract solution alone. The results are shown in Table 5.

When the pH is 4.2 or 4.8, the influenza virus inactivating efficiency did not clearly show an increase dependent on the concentration of the green tea extract solution within the concentration range from 0.1 to 2.5% when the green tea extract solution was used alone.

When 0.115 M arginine was added to each green tea extract solution, the inactivating efficiency increased 3 to 9 times (in the case of pH4.2), and 1.27 to 3.28 times (in the case of pH4.8) based on the respective initial inactivating efficiencies within the concentration of the green tea extract solution of 0.1 to 2.5%. In other words, it was found that the influenza virus inactivating effect of the green tea extract solution is enhanced when the green tea extract solution is used in combination with arginine.

TABLE 5

Virus-inactivating effect by using green tea extract solution and arginine in combination

| pH | Concentration of Green Tea Extract Solution (%) | Concentration of Arginine (M) | Relative Inactivating Efficiency (times) |
|---|---|---|---|
| 4.2 | 0.1 | 0 | 1.00 |
| 4.2 | 0.1 | 0.115 | 9.00 |
| 4.2 | 0.33 | 0 | 0.39 |
| 4.2 | 0.33 | 0.115 | 9.00 |
| 4.2 | 2.5 | 0 | 0.02 |
| 4.2 | 2.5 | 0.115 | 3.00 |
| 4.8 | 0.1 | 0 | 1.00 |
| 4.8 | 0.1 | 0.115 | 2.38 |
| 4.8 | 0.33 | 0 | 0.98 |
| 4.8 | 0.33 | 0.115 | 1.27 |
| 4.8 | 2.5 | 0 | 0.20 |
| 4.8 | 2.5 | 0.115 | 3.28 |

Example 6

Increase of the Virus-Inactivating Effect by Using Arginine Derivative in Combination with Arginine The sample solutions containing 0.005% arginine derivative (cocoyl arginine ethyl ester=CAE, Ajinomoto Co., Ltd.) and arginine at a concentration from 0.058 to 0.287 M were prepared and adjusted to pH 4.0 (25° C.) with 10 mM sodium citrate buffer solution, and the ability of the sample solutions to inactivate herpes virus was determined in the same manner as in Example 1. The inactivating efficiency of each sample solution was expressed as a value relative to the inactivating efficiency obtained by using 0.005% CAE alone (Table 6).

When a sample solution containing 0.005% CAE alone was used for inactivation, the viral titer was reduced to 0.4% of that before inactivation. The inactivation efficiency of a sample solution containing 0.058 M arginine alone was just 0.03 times that of the sample solution containing 0.005% CAE alone. However, when both of them were used in combination, the inactivating efficiency increased 1.13 times. When CAE (0.005%) was mixed with arginine (0.115 M), the inactivating efficiency went up to 20 times. By adding arginine of 0.172, 0.230, and 0.287 M to CAE (0.005%), the inactivating efficiencies were more than 283 times as high as that of the initial inactivating efficiency in any case. In other words, it was found that use of the arginine derivative in combination with arginine can drastically increase the herpes virus inactivating effect.

TABLE 6

Virus-inactivating effect by using arginine derivative and arginine in combination

| CAE Concentration (%) | Concentration of Arginine (M) | Relative Inactivating Efficiency (times) |
|---|---|---|
| 0.005 | 0 | 1 |
| 0 | 0.058 | 0.03 |
| 0.005 | 0.058 | 1.13 |
| 0.005 | 0.115 | 20 |
| 0.005 | 0.172 | >283 |
| 0.005 | 0.230 | >283 |
| 0.005 | 0.287 | >283 |

Example 7

Increase of the Virus-Inactivating Effect by Using Arginine Derivative in Combination with Arginine The sample solutions containing 0.01% or 0.02% arginine derivative (cocoyl arginine ethyl ester=CAE, Ajinomoto Co., Ltd.) and arginine at a concentration of 0 M or 0.115 M were prepared and adjusted to pH 4.8 (25° C.) with 10 mM sodium citrate buffer solution. The influenza virus inactivating effect of each sample solution was determined in the same manner as in Example 5. The inactivating efficiency of each sample solution was expressed as a value relative to the inactivating efficiency obtained by using 0.01% CAE alone (Table 7).

When the sample solution containing 0.01% CAE alone was used for inactivation, the viral titer was reduced to 3.1% of that before inactivation. Addition of 0.115 M arginine to the above-mentioned 0.01% CAE solution drastically increased the virus inactivating effect by 82 times. The inactivating effect of the sample solution containing 0.02% CAE alone was increased just four times. However, by the addition of 0.115 M arginine to the above-mentioned 0.02% CAE sample solution, the inactivating effect was increased by 63 times. It was also found that use of the arginine derivative in combination with arginine can also drastically increase the virus inactivating effect when the pH of the sample solution was 4.8,

TABLE 7

Virus-inactivating effect by using arginine derivative and arginine in combination

| CAE Concentration (%) | Concentration of Arginine (M) | Relative Inactivating Efficiency (Times) |
|---|---|---|
| 0.01 | 0 | 1 |
| 0.01 | 0.115 | 82 |

TABLE 7-continued

Virus-inactivating effect by using arginine derivative and arginine in combination

| CAE Concentration (%) | Concentration of Arginine (M) | Relative Inactivating Efficiency (Times) |
|---|---|---|
| 0.02 | 0 | 4 |
| 0.02 | 0.115 | 63 |

Comparative Example 1

Change in Virus-Inactivating Effect by Mixing Caffeine with Arginine

Sample solutions were prepared by mixing caffeine (Wako Pure Chemical Industries, Ltd.) at a concentration from 0.5 to 2 mM and 0.2 M arginine, and adjusting the solutions to pH 4.0 (25° C.) with 10 mM sodium citrate buffer solution. In the same manner as in Example 1, the inactivating efficiency of each sample solution was expressed as a value relative to the inactivating efficiency obtained by using 0.5 mM caffeine alone (Table 8).

When the sample solution containing 0.5 mM caffeine alone was used for inactivation, the viral titer was reduced to 3.4% of that before inactivation. There was no change in the inactivating efficiency when the concentration of caffeine was increased to 2 mM.

On the other hand, the inactivating efficiency obtained by using 0.2 M arginine alone was 1075 times as high as the inactivating efficiency obtained by using 0.5 mM caffeine alone. However, when caffeine was added at various concentrations to the above-mentioned 0.2 mM arginine solution, the inactivating efficiency did not increase. On the contrary, the inactivating efficiency showed a declining tendency (253 to 717 times). Those results demonstrated that the virus inactivating effect cannot be improved even though caffeine is used in combination with arginine.

TABLE 8

Virus-inactivating effect by using caffeine and arginine in combination

| Compound Name | Concentration of Compound (mM) | Concentration of Arginine (M) | Relative Inactivating Efficiency (times) |
|---|---|---|---|
| Caffeine | 0.5 | 0 | 1 |
| Caffeine | 1 | 0 | 1 |
| Caffeine | 2 | 0 | 1 |
| Caffeine | 0 | 0.2 | 1075 |
| Caffeine | 0.5 | 0.2 | 253 |
| Caffeine | 1 | 0.2 | 717 |
| Caffeine | 2 | 0.2 | 614 |

Comparative Example 2

The inactivating effect by the combined use of caffeic acid and NaCl was examined in the same manner as in Example 1 except that arginine was replaced by 0.2 M NaCl. Sample solutions were prepared by mixing 0.2 M NaCl with caffeic acid (made by Sigma-Aldrich Corporation) at a concentration within a range of 0.1 to 1 mM and adjusting the solutions to pH 4.0 (25° C.) with 20 mM sodium acetate buffer solution. The inactivating efficiency of each sample solution was expressed as a value relative to the inactivating efficiency obtained by using 0.1 mM caffeic acid alone (Table 9).

When the inactivation was carried out using 0.1 mM caffeic acid alone, the viral titer was reduced to 0.13% of that before inactivation. The virus inactivating efficiency drastically decreased 0.01 times when 0.2 M NaCl was added to 0.1 mM caffeic acid. In this case, increase of the concentration of caffeic acid to 0.5 mM and 1.0 mM did not improve the inactivating efficiency at all (respectively 0.009 times and 0.007 times). The inactivating efficiency obtained by using 0.2 M NaCl alone (pH 4.0) was 0.011 times. In this case, the inactivating efficiencies were almost the same as the above even by the addition of caffeic acid at different concentrations. This demonstrated that the characteristics of NaCl were dominant in the inactivating effect.

The recent report revealed that the inactivating effect is conspicuously hindered by the presence of NaCl or sucrose together with the sample to be subjected to virus inactivation when the virus inactivation is carried out under application of high pressure of 200 MPa or more (International Journal of Food Microbiology 130, 61-64 (2009)). The drastic decrease of the virus inactivating effect in the presence of NaCl as shown in Comparative Example 2 is a phenomenon similar to the effect of stabilizing the viruses as observed in the high-pressure virus inactivating treatment.

In contrast to this, the presence of arginine together with other compounds allows the compounds to exhibit the concentration-dependent virus inactivating effect and enhance the inactivating efficiency, as shown in Examples 1 to 7. The above-mentioned results are just the opposite of the stabilizing effect of the salts such as NaCl and polyols as previously reported.

TABLE 9

Virus-inactivating effect by using caffeic acid and NaCl in combination

| Compound Name | Concentration of Compound (mM) | Concentration of NaCl (M) | Relative Inactivating Efficiency (times) |
|---|---|---|---|
| Caffeic acid | 0.1 | 0 | 1 |
| Caffeic acid | 0.0 | 0.2 | 0.011 |
| Caffeic acid | 0.1 | 0.2 | 0.010 |
| Caffeic acid | 0.5 | 0.2 | 0.009 |
| Caffeic acid | 1.0 | 0.2 | 0.007 |

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method of inactivating lipid-envelope viruses on a virus contaminated surface in need thereof, wherein the surface is an outer surface of living tissue of humans or animals or is a surface of a substrate, and wherein said viruses are proliferating on the surface, the method comprising bringing a composition with pH of 3.8 to 5.5 into contact with the virus contaminated surface,
  wherein the composition comprises:
  (A) 0.115M to 0.287M arginine, and
  (B) a component (B) selected from the group consisting of:
    i) 0.01 to 0.5 mM of (−)epicatechin gallate or (−)epigallocatechin gallate;
    ii) 0.01 to 0.1 mM caffeic acid phenethyl ester;

iii) 0.1 to 10 mM dehydroascorbic acid; and
iv) 0.005 to 0.02 mass % of cocoyl arginine ethyl ester; and
wherein said viruses are selected from the group consisting of influenza and herpes.

* * * * *